(12) United States Patent
Yang

(10) Patent No.: US 7,790,380 B2
(45) Date of Patent: Sep. 7, 2010

(54) KITS FOR MULTIPLEXED NUCLEIC ACID ANALYSIS BY CAPTURE OF SINGLE-STRANDED DNA PRODUCED FROM DOUBLE-STRANDED TARGET FRAGMENTS

(75) Inventor: Jiacheng Yang, Hillsboro, NJ (US)

(73) Assignee: BioArray Solutions, Ltd., Warren, NJ (US)

( * ) Notice: Subject to any disclaimer, the term of this patent is extended or adjusted under 35 U.S.C. 154(b) by 0 days.

(21) Appl. No.: 11/437,246

(22) Filed: May 19, 2006

(65) Prior Publication Data

US 2007/0178481 A1 Aug. 2, 2007

Related U.S. Application Data

(63) Continuation of application No. 10/974,042, filed on Oct. 26, 2004, now Pat. No. 7,049,077.

(60) Provisional application No. 60/515,413, filed on Oct. 29, 2003.

(51) Int. Cl.
*C12Q 1/68* (2006.01)
*C12P 19/34* (2006.01)
(52) U.S. Cl. .................................. 435/6; 435/91.2
(58) Field of Classification Search .................. None
See application file for complete search history.

(56) References Cited

U.S. PATENT DOCUMENTS 7,049,077 B2 * 5/2006 Yang .............................. 435/6

FOREIGN PATENT DOCUMENTS

| EP | 1564306 A2 | 8/2005 |
|---|---|---|
| WO | WO 0136679 A2 | 5/2001 |
| WO | WO 03020968 A2 | 3/2003 |
| WO | WO 03034029 A2 | 4/2003 |

OTHER PUBLICATIONS

Molecular Biology Reagents/Protocols 1992, United States Biochemical Corporation, 1991, Cleveland, Ohio, pp. 218-219.*
Kubo, et al. "A Novel, Sensitive and specific assay for abasic sites, the most commonly produced DNA lesion". Biochemistry. vol. 31:3703-3708 (1992).
Weinfeld et al. "Selective hydrolosis by exo-and endonucleases of phosphodiester bonds adjacent to an apurinic site". Nucleic Acids Research. vol. 17, No. 10: 3735-3744 (1989).
LaForge et al. "Detection of single nucleotide polymorphisms of the human mu opioid receptor gene by hybridization or single nucleotide extension on custom oligonucleotide gelpad microchips: potential in studies of addiction". American Journal of Medical Genetics. vol. 96: 604-615 (2000).
Chaudhry et al. Reactivity of human apurinic/apyrimidinic endonucleoase and *Escherichia coli* exonucleoase III with bistranded abasic sites in DNA. The Journal of Biological Chemistry. vol. 272: 15650-15655 (1997).
Wahl et al. "Efficient transfer of large DNA fragments from agarose gels to diazobenzyloxymethyl-paper and rapid hybridization by using dextran sulfate". Proc. Natl. Acad. Sci. USA. vol. 76, No. 8: 3683-3687 (1979).
Lindahl et al. "Rate of chain breakage at apurinic sites in double-stranded deoxyribonucleic acid". Biochemistry. vol. 11, No. 19: 3618-3623 (1972).
Lindahl et al. "Rate of depuriniation of native deoxyribonucleic acid". Biochemistry. vol. 11, No. 19: 3610-3617 (1972).
Proudinikov et al. "Chemical methods of DNA and RNA fluorescent labeling". Nucleic Acids Research. vol. 24, No. 22: 4535-4542 (1996).
Ide et al. "Synthesis and damage specificity of a novel probe for the detection of abasic sites in DNA". Biochemistry. vol. 32: 8276-8283 (1993).
Lhomme et al. "Abasic DNA structure, reactivity and recognition". Biopolymers. vol. 52: 65-83 (1999).
Martinell, J. et al., "Three mouse models of human thalassemia," *Proceedings of the National Acadamy of Sciences of the United States of America*, vol. 78, No. 8: 5056-5060 (1981).
Kelly: Radical-generating coordination complexes as tools for rapid and effective fragmentation and fluorescent labeling of nucleic . . . Analytical Biochem. 311, 103-118 (2002).
Proudnikov: Immobilization of DNA in polyacrylamide gel for the manufacture of DNA and DNA-oligonucleotide microchips. Analytical Biochem. 259, 34-41 (1998).
Zhang: Reproducible and inexpensive probe preparation for oligonucleotide arrays. Nucleic Acid Res. 29 Bavykin:(13), 1-5 (2001).

* cited by examiner

*Primary Examiner*—James Martinell
(74) *Attorney, Agent, or Firm*—Womble Carlyle Sandridge & Rice PLLC

(57) ABSTRACT

A method of fragmentation of double stranded DNA is disclosed for use in nucleic acid analysis, notably in the multiplexed analysis of polymorphisms and mutations. The method produces a multiplicity of labeled sense and anti-sense fragments which are not complementary, and thus do not significantly re-anneal under conditions suitable for hybridization analysis (or capture-mediated elongation analysis) of the polymorphisms and/or mutations. The fragments display a desired or predicted length distribution. Cleavage sites can be selected such that the fragments are short, yet long enough to allow discrimination among fragments in an assay, and as a matter of statistical probability, such that the majority of fragments contain at least one labeled nucleotide to facilitate detection.

10 Claims, 8 Drawing Sheets

Lane

1: 50 bp DNA ladder
2: PCR products without cleavage
3: 0 min depurination
4: 10 min at 37°C depurination
5: 13 min at 37°C depurination
6: 15 min at 37°C depurination
7: 17 min at 37°C depurination
8: 20 min at 37°C depurination
9: 25 min at 37°C depurination
10: 25 min at 37°C, then 15 min at 56°C depurination Step 1

Step 2

Step 3

Step 4

Step 1

Step 2

Step 3

Step 4

SEQUENCE LISTING

<160> NUMBER OF SEQ ID NOS: 1

<210> SEQ ID NO 1
<211> LENGTH: 268
<212> TYPE: DNA
<213> ORGANISM: Homo sapiens

<400> SEQUENCE: 1

```
gctcccactc catgaggtat ttctacacct ccgtgtcccg gcccggccgc ggggagcccc      60
gcttcatctc agtgggctac gtggacgaca cccagttcgt gaggttcgac agcgacgccg     120
cgagtccgag agaggagccg cgggcgccgt ggatagagca ggaggggccg gagtattggg     180
ccggaacaca cagatctaca aggcccaggc acagactgac cgagagagcc tgcggaacct     240
gcgcggctac tacaaccaga gcgaggcc                                        268
```

KITS FOR MULTIPLEXED NUCLEIC ACID ANALYSIS BY CAPTURE OF SINGLE-STRANDED DNA PRODUCED FROM DOUBLE-STRANDED TARGET FRAGMENTS

RELATED APPLICATIONS

This application is a continuation of U.S. application Ser. No. 10/974,042 (now U.S. Pat. No. 7,049,077) filed on Oct. 26, 2004, which claims priority to Provisional Application No. 60/515,413, filed Oct. 29, 2003, priority to both of which is claimed.

BACKGROUND

In a conventional multiplexed reverse dot blot hybridization assay protocol used in the process of detecting the presence of particular alleles in a sample, selected loci in the double-stranded genomic DNA are first amplified using pairs of forward and reverse primers, and one designated strand of each of the double-stranded amplicons is removed, for example by enzymatic digestion or magnetic separation. Only the remaining strands, preferably labeled, are placed in contact with a set of cognate probes, spotted or otherwise placed on a substrate, such as a strip of nitrocellulose, or displayed on encoded microparticles in preparation for a hybridization assay. Hybridization is typically detected based on the presence of label associated with the set of captured targets or with the corresponding probes. Decoding allows determination of the subsequences of the strands captured by particular probes, indicating that the capturing probes are complementary to such subsequences.

Removal of the designated strands is intended to improve the efficiency of capture of the remaining strands to probes, by eliminating strand-strand re-annealing, a process which competes with annealing to cognate capture probes, and would otherwise take place without strand selection and removal in the protocol.

Strands can be removed by digestion, wherein strands selected for removal are first phosphorylated, and then enzymatically digested using a digestion enzyme such as λ-endonuclease for the phosphorylated strands. Strands can also be removed by magnetic separation. Both digestion as well as magnetic separation add cost and labor to the assay protocol. A preferable alternative would be to generate single-stranded fragments from amplicons, thereby eliminating the need for digestion or magnetic separation.

Several methods are known to generate single-stranded fragments of random length from double-stranded DNA. In the conventional Maxam and Gilbert sequencing method (A. Maxam and W. Gilbert, PNAS 74, p. 560, 1977), fragments of double-stranded DNA are generated by selective chemical degradation of multiple copies of the DNA species to be sequenced. Conditions are adjusted to produce fragments of all possible lengths; that is, fragments can be separated into fractions differing from one another in length by only a single base. When ordered, the sequence of fractions with their respective terminal bases represents the sequence of the original DNA species.

E. Southern et al. have also generated random-sized single-stranded fragments from double-stranded DNA to facilitate the transfer of DNA from agarose gels for blotting on membranes for further analysis by hybridization with oligonucleotide probes, in what represents a dot blot format. Conditions are adjusted to produce fragments that are sufficiently short to minimize entanglement within the gel.

To date, no one has suggested the use of amplicon fragments without strand digestion or separation for use in reverse dot blot hybridization assay formats. Thus, there is no suggestion that, for multiplexed analysis of polymorphisms (MAP), the use of a complex mixture of highly heterogeneous target fragments is preferable to the use of a single, or at most a few, target sequences. Further, to use fragmentation for MAP, unless conditions are adjusted correctly, some or all polymorphic sites may be eliminated, or labeling may be impractical, and none of these problems or their solutions have been suggested.

One conventional method of labeling amplicons is to perform the amplification with 5'-terminally labeled primers so as to produce end-labeled amplicons. This end-labeling method requires that labeled strands remain intact because, after fragmentation, none but a small portion of the fragments containing the 5-terminus will be labeled. Therefore, a different method of labeling is needed where the amplicons are to be fragmented.

SUMMARY

A method of fragmentation of double stranded DNA is disclosed for use in nucleic acid analysis, notably in the multiplexed analysis of polymorphisms and mutations. The method produces a multiplicity of labeled sense and anti-sense fragments which are not complementary, and thus do not significantly re-anneal under conditions suitable for hybridization analysis (or capture-mediated elongation analysis) of the polymorphisms and/or mutations. The fragments display a desired or predicted length distribution. Cleavage sites can be selected such that the fragments are short, yet long enough to allow discrimination among fragments in an assay, and as a matter of statistical probability, such that the majority of fragments contain at least one labeled nucleotide to facilitate detection. That is, conditions are adjusted so as to produce a fragment length distribution which generates a selected linear density of strand labeling, by inclusion of labeled nucleotides. In an alternative embodiment, the majority of fragments are comparable in length to the length of the cognate capture probes.

Double stranded DNA (or double stranded amplicons derived from double stranded DNA by amplification) is transformed into a set of sense and anti-sense fragments by strand cleavage at a multiplicity of sites which are randomly distributed along each strand in order to produce fragments which are not fully complementary. This can be accomplished by simply cleaving at the same base on each strand. These fragments are then placed in contact, under annealing conditions, with probes which are fully complementary to at least some of the predicted fragments. Hybridization events are detected, and based on the results, the presence or absence of particular oligonucleotide segments in the sample is determined.

The advantages of this method are:

(i) eliminating the step of post-PCR strand selection;

(ii) enhancing the target capture efficiency by selecting the density of fragmentation sites so as to generate relatively short targets having minimal secondary structure and display a high effective affinity, as detailed in co-pending application, entitled: "Optimization of Gene Expression Analysis using Immobilized Capture Probes," filed on Oct. 28, 2004, incorporated by reference.

(iii) permitting the use of both sense and anti-sense capture probes for the interrogation of polymorphic sites on both strands. This is an aspect of design which is advantageous in a multiplexed assay, because it may be desirable to use particular probes which selectively bind to either sense or antisense strands, to avoid cross-hybridization with non-cognate targets. See, e.g., U.S. application Ser. No. 10/847,046, filed May 17, 2004 "Hybridization-Mediated Analysis of Polymorphisms (hMAP)," incorporated by reference. Further, the inclusion of the anti-sense probe along with the corresponding sense probe enhances the capture efficiency because the anti-sense probe removes from the solution a portion of sense target thereby further reducing the degree of strand re-annealing in solution.

One can incorporate, during the PCR amplification which generates the amplicons, the label which ultimately identifies the hybridized targets. A consideration here is that the label must be incorporated with sufficient frequency during PCR such that the probability is that all the resulting fragments incorporate at least some label. Necessarily, therefore, where the fragments are shorter, the frequency of label must be higher in each of the fragments.

As an optional step, following hybridization and identification of the hybridized targets in the sample, one can verify the reliability of the results of hybridization using a capture-mediated and elongation analysis. In this step, a new set of probes is designed, some of which may be shorter than or complementary to the initial probe set used for hybridization analysis. The shorter probes would be needed in the cases where in the expected targets, there is more than one polymorphic locus (or subsequence corresponding to a polymorphic locus) along the length of the fragment. In order to achieve a reliable result in capture-mediated elongation analysis, a terminal probe nucleotide must align with each polymorphic nucleotide ("SNP"). See U.S. application Ser. No. 10/271,602, entitled "Multiplexed Analysis of Polymorphic Loci by Concurrent Interrogation and Enzyme-Mediated Detection," filed Oct. 15, 2002, incorporated by reference.

In addition, a complementary probe may be used if it aids in avoiding cross-hybridization among targets in the set. Complementary probes would hybridize to the complementary target strand (either the sense or anti-sense strand) of the target strand hybridizing with the initial probe set.

Capture-mediated elongation analysis is desirable to increase reliability of the assay results because with hybridization analysis alone (using only an initial target set) false-positives are generated by cross-hybridization. Following the capture-mediated elongation analysis, the results can be compared with the hybridization-mediated analysis, thereby further increasing the reliability. The last comparison step can be performed using a program and software.

The foregoing methods are described below with reference to the drawings.

DETAILED DESCRIPTION

Figure 1:
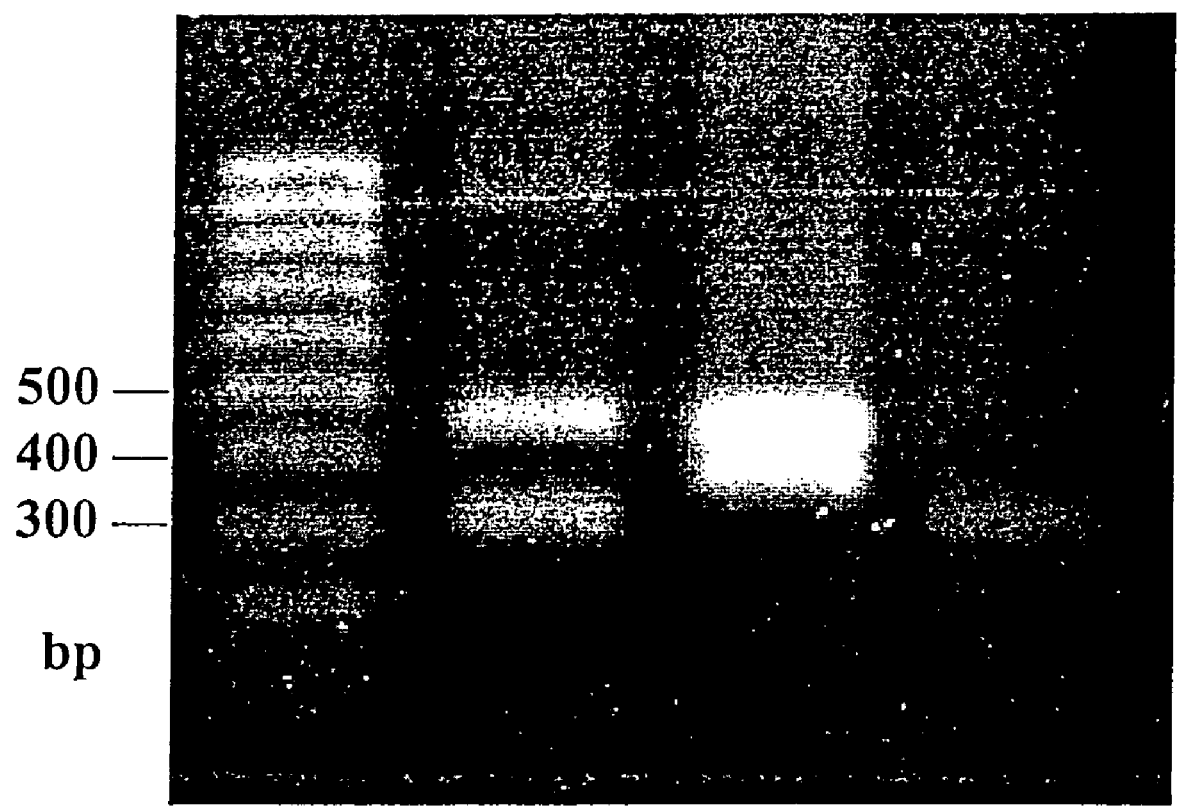
FIG. 1 shows stained PCR products from genomic DNA, visualized on agarose gel under UV illumination.

To perform the methods set forth above, a double-stranded DNA sample, for example, genomic DNA, is first isolated. Certain portions, representing loci of interest, are amplified using PCR. Thereafter, the complementary sense and anti-sense strands can be placed under conditions permitting annealing, or, they can be placed into a gel which keeps the complementary strands separated. In either case, they are eventually annealed into double-stranded DNA amplicons. In the next step, the two complementary strands are cleaved at non-complementary base pairs, to generate sense and anti-sense strands that are only partially complementary. Fully complementary strands would anneal with each other when placed under annealing conditions in contact with a probe array, thereby competing with probe annealing and affecting the assay results.

One well-known method to cleave the sense and anti-sense amplicon strands at particular bases which are not complementary is to randomly nick the purine bases on the amplicons using hydrochloric acid, thereby depurinating these bases. The nicked double stranded DNAs are then heat denatured in alkaline solution thereby generating single-stranded non-complementary DNA fragments. The greater the extent of the depurination, the shorter the length of the resulting single-stranded DNA fragments following the depurination.

As a step in the PCR amplification of double-stranded DNA, it is advantageous to incorporate the label which will ultimately be used in identifying particular strands which hybridize to a probe set. One method to accomplish this is to add labeled deoxynucleotides (or dideoxynucleotides) into the PCR reaction mix to label both amplicon strands during the reaction. Another method is to add biotinylated bases during the PCR, which are then coupled with fluorescent-labeled streptavidin to label at such bases. It is preferred to biotinylate the Cytosine rather than Adenine base nucleotides, as Adenine bases will be depurinated during the depurination step, thereby causing loss of the labeling. As noted above, the labeling frequency must be high enough to ensure that even the shortest fragments one wishes to detect have label incorporated. Labeling during the PCR is advantageous for single-stranded DNA generated by fragmentation, as otherwise each strand would need to be labeled individually in a post-PCR processing step, which would be expensive and time-consuming.

As an additional step, following the hybridization, the results can be verified or refuted to increase reliability if a capture-mediated elongation reaction, as described above, is performed on the cleaved amplicons. The capture-mediated elongation reaction can be performed using shorter or complementary probes to those in the initial set, as described above.

The Examples below further illustrate the methods set forth herein.

Example 1

PCR Amplification

Genomic DNA isolated from human tissue and cells are used as templates in a polymerase chain reaction (PCR).

Oligonucleotides flanking HLA Class I and II genes are used as forward and reverse primers for amplification of specific loci, or specific gene segments. More than one pair of primers could be used in PCR for amplification of multiple loci. In addition, primers may contain degenerate bases for priming of genomic DNA at polymorphic sites. PCR is performed according to the well-known methods.

Preferably, at least one type of ligand-labeled deoxynucleotide is added into the PCR reaction mixture, to generate amplicons where both strands are labeled. The ligand could be a fluorescent dye or a molecule such as biotin, which can be coupled to a label after the reaction.

PCR is performed using a programmable thermocycler. An aliquot of the PCR products are run on agarose or polyacrylamide gel using electrophoresis, with DNA ladders included in the gel as markers. DNAs in the gel are stained with ethedium bromide, and visualized on a UV transluminator to verify the integrity and yield of the PCR amplicons. For example, exon 2 and exon 3 of A and B loci were amplified in multiplexed PCR by using two sets of primers. Exon 2 of DR locus was amplified using one set of primers. PCR products were biotinylated on both strands with a density of more than one biotinylated nucleotide for each 20 bases of the amplicons. Aliquots of the PCR products were run on agarose gel followed by ethedium bromide staining. The stained PCR products can be visualized on the agarose gel under UV illumination, in FIG. 1.

Example 2

Post PCR Sample Processing

Labeled Class I and Class II PCR products are processed into single stranded DNA fragments by chemical cleavage and denaturization. Briefly, the PCR products are treated with hydrochloric acid to depurinate, as is well-known (see, e.g., M. H. Caruthers et al., in Genetic Engineering: Principles and Methods, J. K. Setlow et al., Eds. (New York: Plenum Press, 1982)). Double stranded DNA is randomly nicked at the purine bases, i.e. adenine and guanine in the presence of hydrochloric acid. The nicked double stranded DNAs are heat denatured at 94° C. in alkaline solution resulting in generation of single stranded DNA fragments. The extent of depurination directly correlates to the size of the single stranded DNA fragments.

Depurination of the PCR amplicons of the Class I and II genes was optimized to obtain small single stranded DNA fragments that, based on a probability determination, would contain at least one biotinylated nucleotide. A size distribution of the cleavage products separated on polyacrylamide gel showed that most of the single stranded DNA fragments were approximately 75 bases long. Each of the DNA fragments should, therefore, contain approximately two biotinylated nucleotides, in accordance with the conditions described in Example 1.

Figure 2:
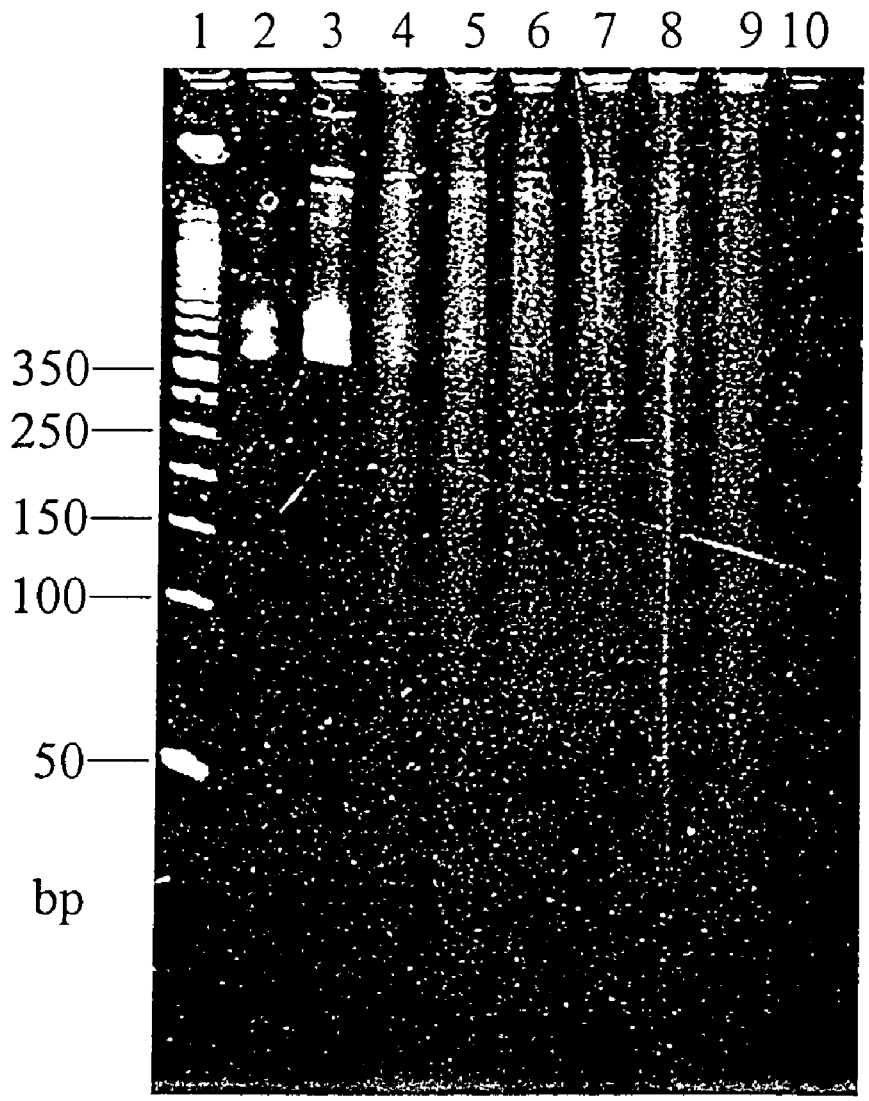
FIG. 2 shows labeled Class I and Class II HLA PCR products which have been processed into single stranded DNA fragments by chemical cleavage and denaturation.
Figure 3A:
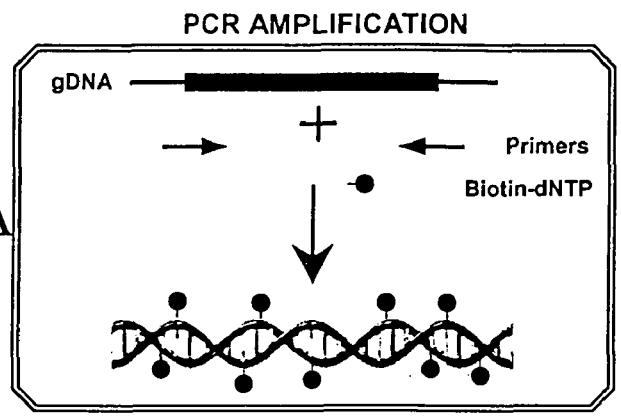
FIGS. 3A-3D illustrates steps involved in carrying out a hybridization-mediated assay using the methods set forth herein.
Figure 3B:
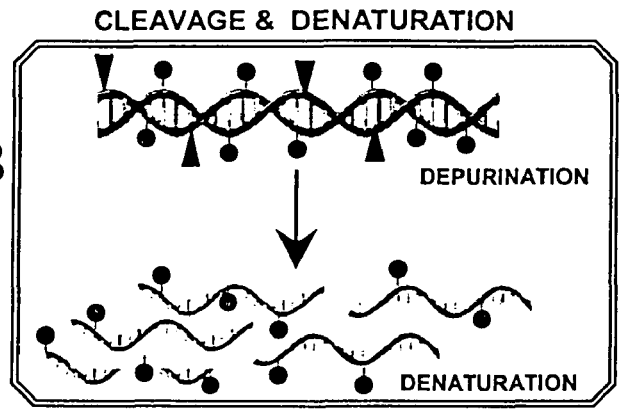
Figure 3C:
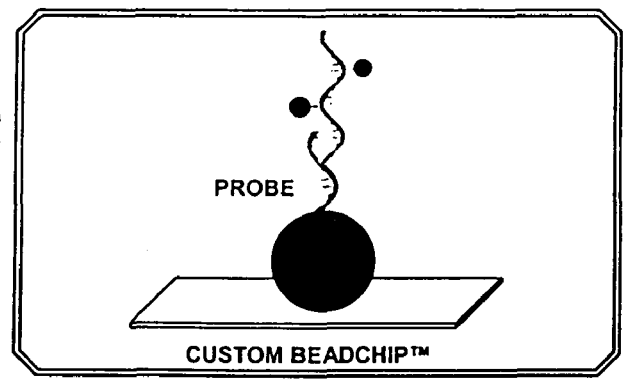
Figure 3D:
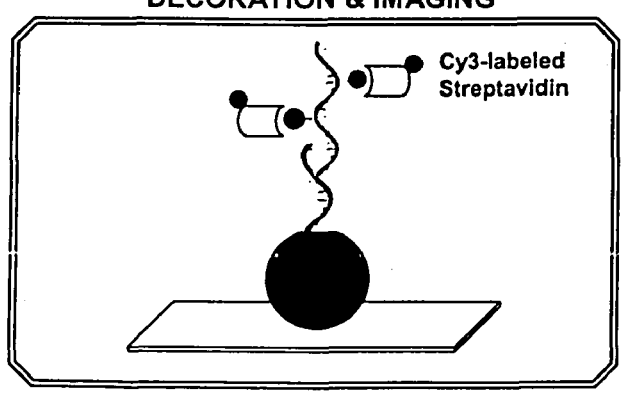

A time course experiment was performed to optimize depurination conditions. Biotinylated PCR products for exon 2 and 3 of the B locus were incubated with specific amounts of hydrochloric acid and incubated in a water bath for increasing periods of time, followed by addition of sodium hydroxide and heat denaturing. The chemically cleaved PCR products were run on 8% urea sequencing to separate the digested products, followed by ethidium bromide staining. The cleaved products were visualized on a UV transluminator (FIG. 2), which demonstrate that the amount of small cleavage products increases as depurination time increase (FIG. 2).

Example 3

On Chip Hybridization Assay

Processed PCR products prepared as described in Example 2 were heat denatured to obtain large numbers of single stranded DNA fragments. After denaturing, the samples are snap frozen on ice to preserve DNA fragments in a single-stranded state. The DNA samples are then mixed with a hybridization buffer for on-chip hybridization to complementary oligonucleotide probes, where different probe types are each immobilized on differently encoded microparticles, and the microparticles are placed in an array on a solid substrate (a "BeadChip™"). See, e.g., U.S. application Ser. No. 10/204,799: "Multianalyte Molecular Analysis Using Application-Specific Random Particle Arrays," filed on Aug. 23, 2002, incorporated by reference.

The hybridization conditions and the ionic strength of the hybridization buffer are conventional in the art. Preferably, on-chip hybridization is carried out in a temperature and humidity-controlled incubator, for fast and efficient reaction dynamics. See U.S. patent application: "Controlled Evaporation, Temperature Control and Packaging for Optical Inspection of Biological Samples," Ser. No. 10/870,213, filed Jun. 17, 2004.

Following hybridization, unbound labeled DNA is removed by intensive washing. Where the oligonucleotides are bound with ligands, such as biotin, rather than fluorescent dyes, the assay chips are incubated with staining solution containing fluorescent-labeled molecules that have a high affinity for the ligands. For example, one can use fluorescently-labeled streptavidin for binding to the biotinylated DNA fragments.

If there is significant cross-hybridization, the labeled DNA targets may be captured by more than one type of probe, and associate with more than one type of encoded microparticle on the BeadChips.

As shown in FIG. 3, a typical hMAP BeadChip assay would have four steps as follows: Step 1, PCR amplification of genomic DNAs in the presence of labeled dNTPs, such as biotinylated-dATP and biotinylated-dCTP. Both strands of the PCR products are labeled in the PCR reaction. Step 2, the labeled PCR products were depurinated in the present of hydrochloric acid followed by heat denaturing in alkaline solution. Step 3, the fragmented single-stranded DNA targets were used as targets for a BeadChip assay. Step 4, the captured targets on the beads were detected by incubation with fluorescent-labeled ligands that have high affinity to the labels, such as Cy3 conjugated streptavidin for detection of the biotinylated targets, followed by READ detection (FIG. 3).

Figure 4:
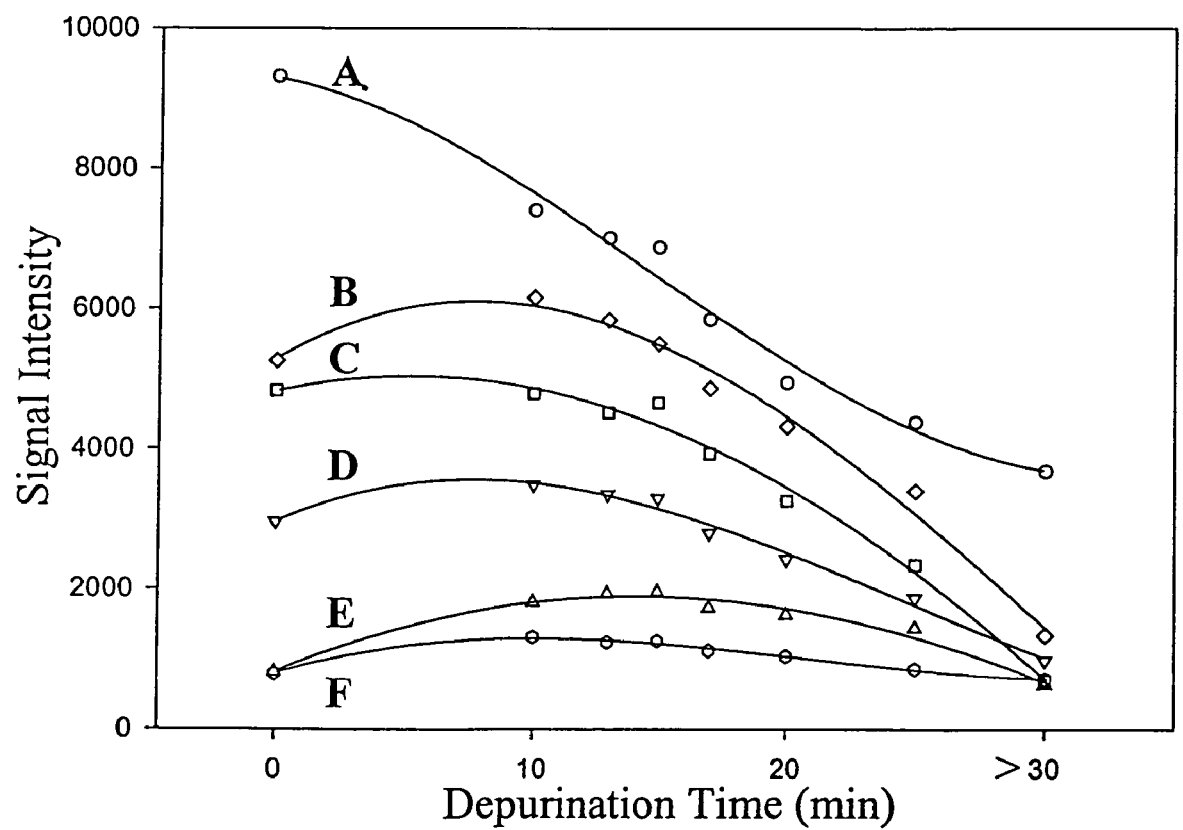
FIG. 4 shows an illustration of intensity vs. depurination time for binding of several targets.
Figure 5A:
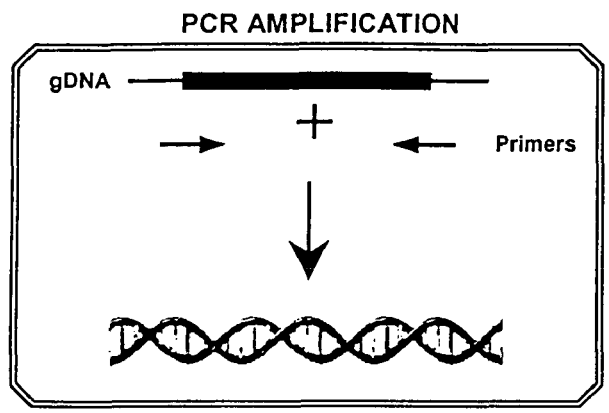
FIGS. 5A-5D illustrates steps involved in carrying out a capture and elongation-mediated assay using the methods set forth herein.
Figure 5B:
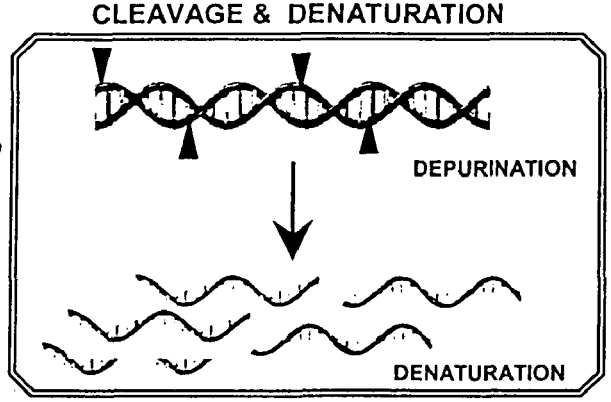
Figure 5C:
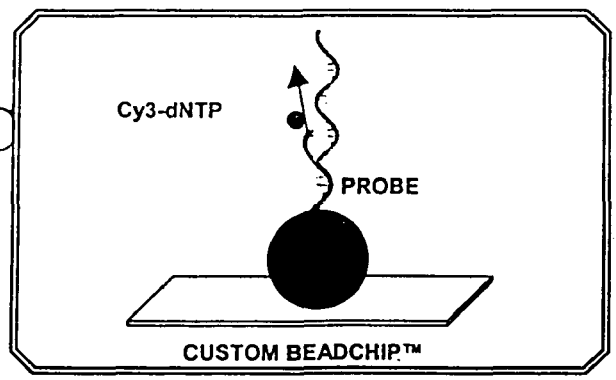
Figure 5D:
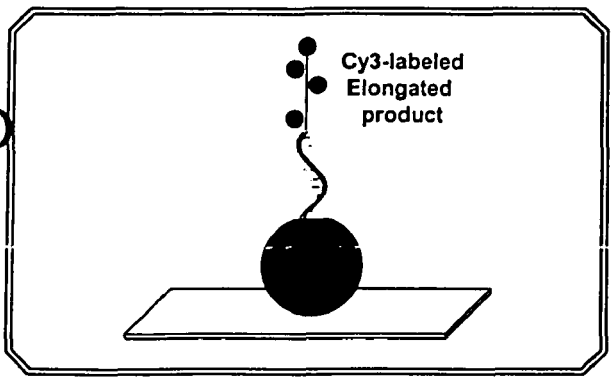

The cleavage DNA products described in Example 2 were used in a BeadChip hMAP assay. Briefly, each of the depurination treatment products, i.e., those resulting from 0, 10, 13, 15, 17, 20, 25, and >25 min depurination, was used as a target in the hMAP BeadChip assay. Hybridization intensities of the targets to a panel of sequence-specific probes were analyzed. As shown in FIG. 4, intensity for probe A and probe C decreases as depurination time increases, suggesting increasing cleavage of long DNA targets into smaller fragments from the depurination. However, intensities for Probes B, D, E and F first increase in partial depurination, then decrease in further depurination, suggesting partial cleavage results in release of certain target sequences that were unavailable in long DNAs due to other factors, such as secondary structure of the targets (FIG. 4).

Example 4

Preparation of Custom Beadchip

DNA oligonucleotide probes used in the hybridization-mediated assay may contain a terminal reactive group, an internal spacer molecule, and a stretch of nucleotides that are complementary to target DNAs of interest. The oligonucleotide probes can be complementary to the sense strand or the antisense strand of the DNA molecules. One or the other strand is selected to reduce cross-hybridization.

After coupling DNA oligonucleotides to the color encoded microparticles, different oligonucleotide-functionalized microparticles are combined into one tube for assembly of a random planar bead array on a silicon wafer (or BeadChip). In HLA molecular typing, each BeadChip should contain multiple sense and antisense probes for specific locus of Class I and Class II molecules. BeadChips for different loci may be bound into a common chamber for hybridization reaction.

Example 5

Capture-Mediated Elongation Analysis

As discussed above, following the hybridization-mediated analysis, results may be confirmed or refuted using capture-mediated elongation reactions. As shown in FIG. 5, a typical eMAP BeadChip assay using chemically cleaved DNA targets should have four steps as follows: Step 1, PCR amplification of genomic DNAs. Step 2, PCR products are depurinated in the presence of hydrochloric acid followed by heat denaturing in alkaline solution. Step 3, the fragmented single-stranded DNAs are used as targets for hybridization to sequence-specific probes followed by an elongation reaction in the presence of fluorescent-labeled dNTPs, such as Cy3-labeled dATP and dCTP. Step 4, the target templates are removed by intensive washing followed by READ detection of elongated probes (FIG. 5).

Example 6

Sense and Antisense Probes in a Multiplexed hMAP Assay

Figure 6:
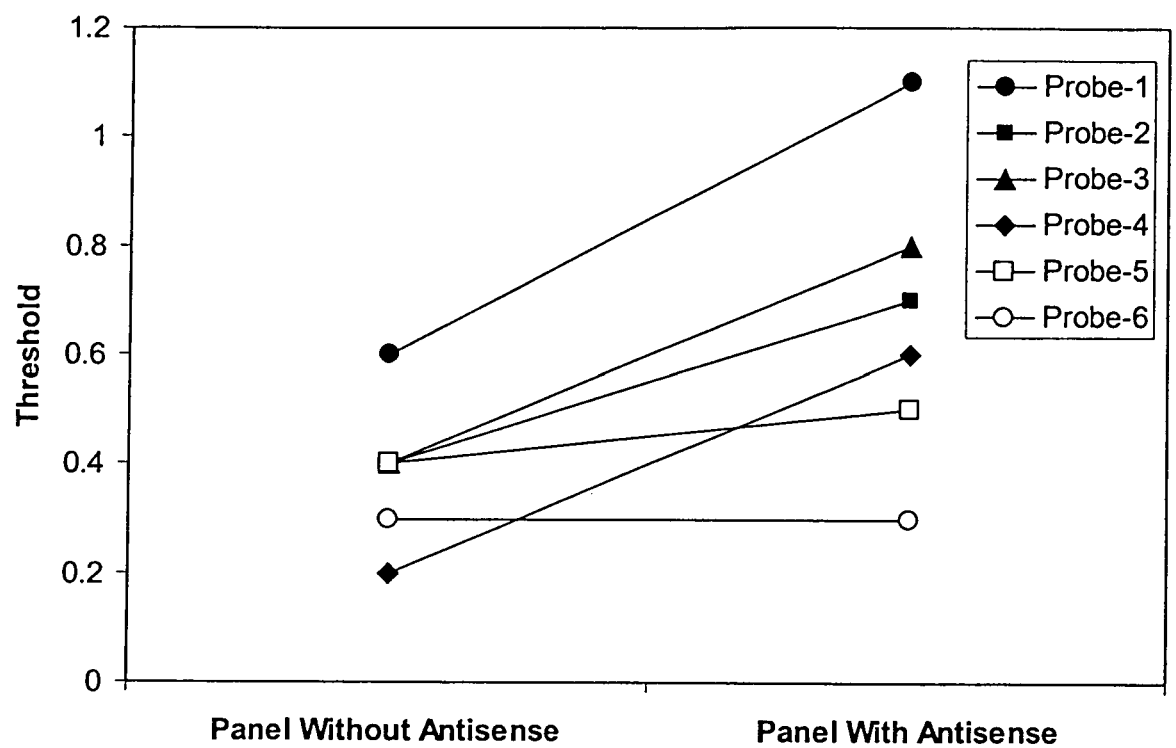
FIG. 6 shows a titration of threshold vs. probes for six different sense probes.

The chemically cleaved DNA targets described herein can be hybridized to a panel of multiple oligonucleotide probes in multiplexed assay format, e.g., one can assay for HLA genes in such a format. In such a multiplexed assay, the oligonucleotide probes may contain capture sequences complementary to either the sense or antisense strands of target HLA subsequences. When such assay was used in screening a set of human DNA samples of known genotypes, probe signal to positive control signal ratio (the "signal ratio") can be determined in each sample for each of the probes of the probe set. A threshold can be arbitrarily set on the signal ratio to distinguish "perfect match," between probe and target, from "mismatch." By binding to the complementary strand of the target DNAs, addition of antisense probes in the panel can enhance capturing efficiency of the sense probes in the multiplex hMAP assay. Experimentally, it was shown that addition of antisense probes did not reduce the capturing efficiency of any of the sense probes and in fact capturing efficiency improved when the antisense probes were added (results not shown). An assay of sense probes only is shown in FIG. 6.

Example 7

Modeling of DNA Fragmentation

In this example the modeling of two different aspects of the DNA fragmentation process is addressed, i.e., the fragment size distribution of single stranded DNA (of a known composition) and the survival probability of a particular stretch of DNA in the strand following fragmentation. The value of this analysis is two fold. First, it identifies how the fragment size evolves as a function of % fragmentation. Second, by modeling fragment size distribution, it provides a unique way of estimating the survival probability of a target region in the DNA strand of interest. This has important implications as far as design of capture probes are concerned because only that fraction of fragments containing the intact subsequences of interest, or those fragments allowing substantial probe-target overlap, can successfully anneal to the capture probe. Fragments with smaller mutual overlap regions denature before detection or extension takes place. Also, since fragment size distribution and the % of strands containing an uncut region of interest are both experimentally accessible quantities, this method provides a unique way of matching experimental with modeling results, possibly allowing to quantify important parameters in the model.

For the purpose of the simulation, it is assumed that the experimental fragmentation protocol outlined above generates a random distribution of polynucleotide fragments. Random fragmentation implies that each cleavable nucleotide-nucleotide bond has an equal probability, $P_{cut}$, of being broken. This assumption is reasonable because the fragmentation protocol is not known to be sequence-dependent and fragments all the available A and G's in an unbiased fashion. Another assumption is that the bond breaking events are independent and hence the order in which the fragments are produced does not affect their probabilities of occurrence. Simulations were performed using a single stranded HLA B Exon 2 amplicon, which is 268 bases long. The sequence is shown below (SEQ ID NO. 1).

```
  1 GCTCCCACTC CATGAGGTAT TTCTACACCT CCGTGTCCCG GCCCGGCCGC
 51 GGGGAGCCCC GCTTCATCTC AGTGGGCTAC GTGGACGACA CCCAGTTCGT
101 GAGGTTCGAC AGCGACGCCG CGAGTCCGAG AGAGGAGCCG CGGGCGCCGT
151 GGATAGAGCA GGAGGGGCCG GAGTATTGGG CCGGAACACA CAGATCTACA
201 AGGCCCAGGC ACAGACTGAC CGAGAGAGCC TGCGGAACCT GCGCGGCTAC
251 TACAACCAGA GCGAGGCC
```

Methodology:
1) Given parameters $P_{cut}$ ($P_{cut}$=% fragmentation) and strand sequence.
2) Divide the sequence into regions differentiable by bonds which can be broken and which cannot be broken by the protocol. The total number of fragmentable bonds is denoted as $n_F$. Adjacent nonfragmentable bonds are lumped together as unfragmentable regions flanked by fragmentable bonds.
3) Create an ensemble of N sequences, each containing $n_F$ regions (fragmentable). Typically N=1000.
4) Generate 2 vectors of uniform random numbers, $R_1$ and $R_2$, between 0 and 1, each of size $N_{cut}=(n_F*P_{cut}*N)/100$, where $N_{cut}$ denotes the total number of bonds in the ensemble that are to be broken. From the first vector, determine random locations within a sequence where cuts occur. Thus, for the vector $R_1$, the cut locations are calculated by evaluating the quantity $(n_F*R_1)$. From the second vector, the particular replicate in the ensemble which is cut, is determined as follows, $(N*R_2)$. Thus, for each cut, i, to be operated on the sequence, a set of two numbers are generated $(f_i, n_i)$ where $n_i$ is the replicate number on which the cut is to be made and $f_i$ is the fragmentable bond in that replicate which is to be cut. However, each set of $(f_i, n_i)$ generated may not be unique. Thus, a particular bond on a particular replicate may be revisited during the exercise. Once a given bond is designated as broken, the repeated set $(f_i, n_i)$, defining the location of that bond, is discarded whenever it is encountered. Thus in practice the total number of bonds broken during the exercise is $n_{cut} \leq N_{cut}$.
5) The number of bases (connected lumped fragmentable regions and unfragmented regions) flanked either by broken bonds or the termini of the sequence are calculated to given the fragment size distribution.

Figure 7:
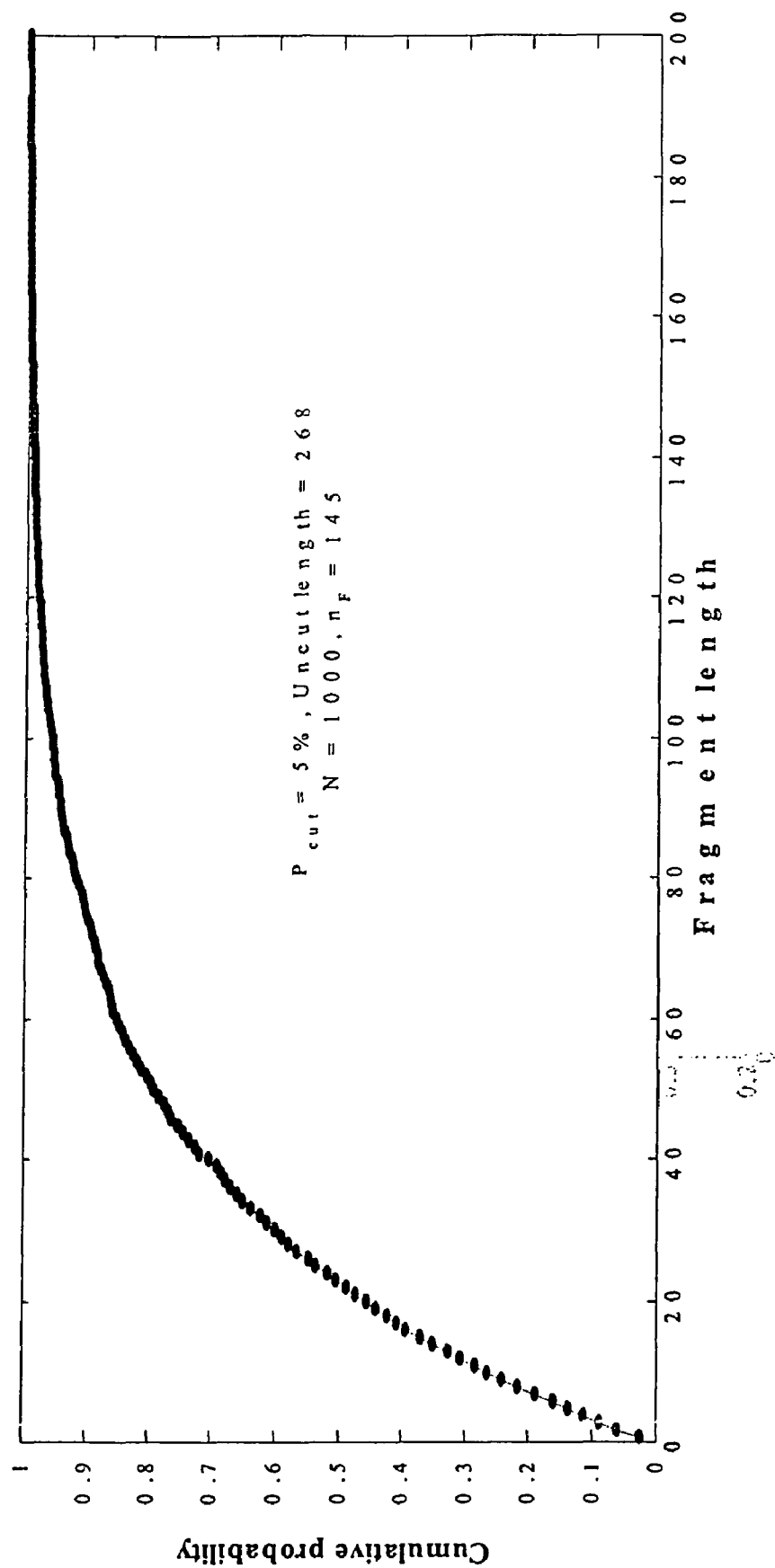
FIG. 7 shows the cumulative size distribution of the fragments resulting from the chosen DNA strand with a $P_{cut}$ value of 5%.
Figure 8:
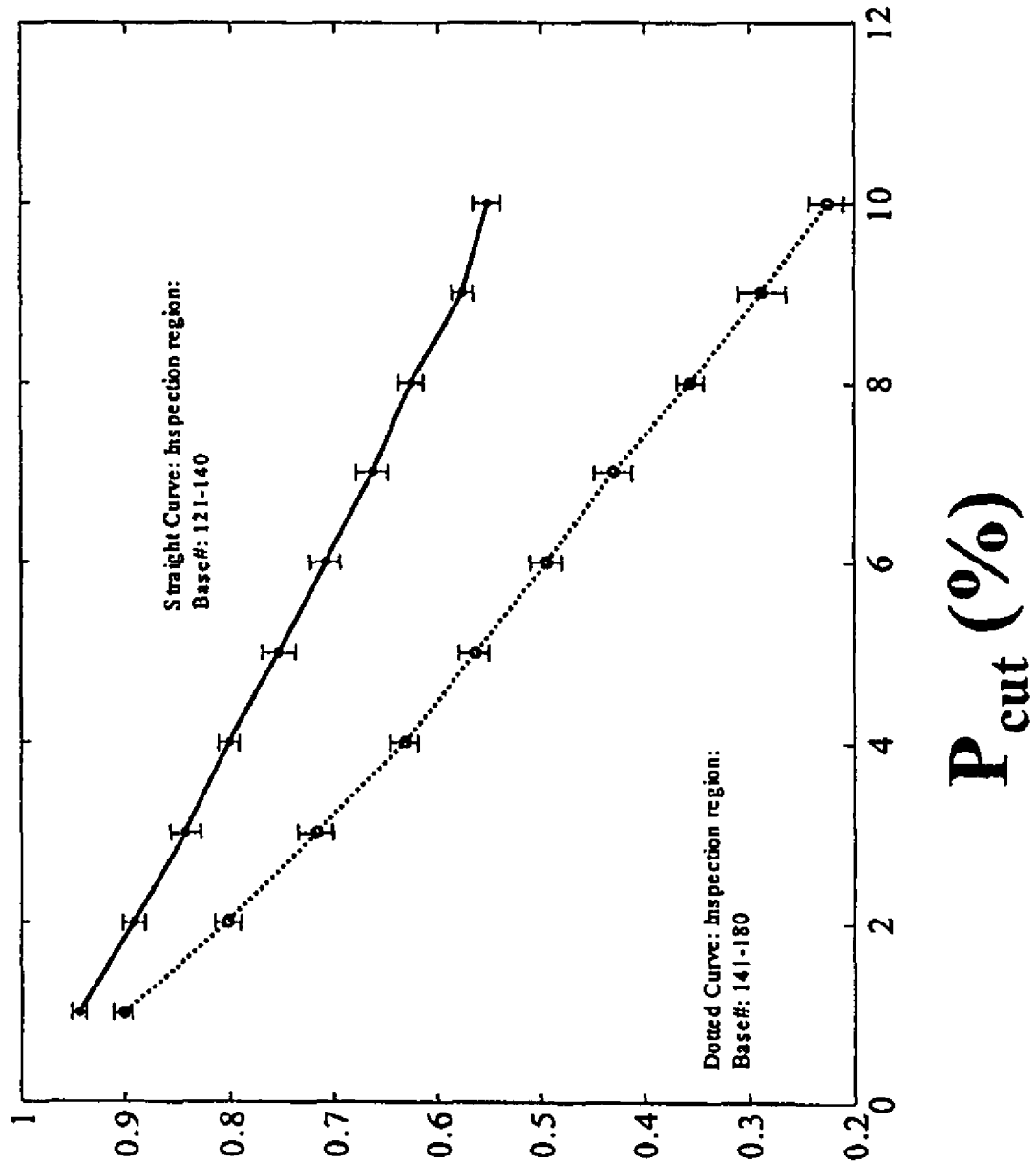
FIG. 8 shows the survival probability of two different regions of unequal length but the same ratio of fragmentable to unfragmentable bonds in the chosen DNA strand.

FIG. 7 shows the cumulative size distribution of the fragments resulting from the chosen DNA strand with a $P_{cut}$ value of 5%. The figure illustrates that small fragments are more ubiquitous than large ones (with fragments of length less than ~20 bases constituting 50% of the final mixture of fragments). FIG. 8 shows the survival probability of two different regions of unequal length but the same ratio of fragmentable to unfragmentable bonds in the chosen DNA strand.

It should be understood that the terms, expressions and examples used herein are exemplary only, and not limiting, and that the scope of the invention is defined only in the claims which follow, and includes all equivalents of the subject matter of the claims. Process and method steps in the claims can be carried out in any order, including the order set forth in the claims, unless otherwise specified in the claims.

The invention claimed is:

1. A method for detecting particular nucleotide sequences in a double-stranded oligonucleotide sample, comprising:
    amplifying segments of the sample with unlabeled primers in the presence of labeled nucleotides to generate labeled double stranded amplicons;
    cleaving the double-stranded amplicons at a multiplicity of sites which are randomly distributed along each strand to produce fragments which are not fully complementary to one another;
    mixing the fragments with a hybridization buffer;
    placing the fragments in contact with a set of single-stranded oligonucleotides under annealing conditions, wherein single-stranded oligonucleotides in the set are complementary to the fragments or to subsequences of the fragments; and
    detecting hybridization between said set of single-stranded oligonucleotides and the fragments.

2. The method according to claim 1, wherein the labeled nucleotides are fluorescently labeled.

3. The method according to claim 1, wherein the labeled nucleotides comprise biotin.

4. The method of claim 3, wherein detecting comprises contacting the fragments with labeled streptavidin.

5. The method according to claim 1, wherein cleaving comprises depurination of the amplicon by contacting the amplicon with hydrochloric acid then heat-denaturing to generate single-stranded DNA fragments.

6. The method of claim 1, wherein fragment length is controlled by controlling the pH of the hydrochloric acid, time of exposure to the hydrochloric acid and reaction temperature.

7. The method of claim 6, wherein fragment length is adjusted so as to generate sense and/or anti-sense fragments comparable in length to the single-stranded oligonucleotides.

8. The method of claim 1, wherein the single-stranded oligonucleotides are DNA.

9. The method of claim 1, wherein the double-stranded oligonucleotide sample is genomic DNA.

10. The method of claim 1, wherein the double-stranded oligonucleotide sample includes genetic loci of interest.

* * * * *